United States Patent [19]

Krauter

[11] Patent Number: 4,697,576
[45] Date of Patent: Oct. 6, 1987

[54] ENDOSCOPE FORCEPS ELEVATOR CABLE SEAL

[75] Inventor: Allan I. Krauter, Syracuse, N.Y.

[73] Assignee: Welch Allyn, Inc., Skaneateles Falls, N.Y.

[21] Appl. No.: 830,087

[22] Filed: Feb. 18, 1986

[51] Int. Cl.$^4$ ............................................. A61B 1/00
[52] U.S. Cl. ..................................................... 128/4
[58] Field of Search ...................................... 128/4–8; 73/151, 27 R; 271/1; 337/231

[56] References Cited

U.S. PATENT DOCUMENTS

| 4,150,353 | 4/1979 | Huber et al. | 337/231 |
| 4,190,041 | 2/1980 | Chikama | 128/4 |
| 4,198,959 | 4/1980 | Otani | 128/5 |
| 4,589,403 | 5/1986 | Ouchi et al. | 128/4 |

FOREIGN PATENT DOCUMENTS 2817922  10/1978  Fed. Rep. of Germany .......... 128/4

Primary Examiner—Kyle L. Howell
Assistant Examiner—Max F. Hindenburg

[57] ABSTRACT

The control cable for a rockable forceps elevator of a side-looking endoscope has an elastomeric sleeve covering the exterior part of the cable from the endoscope head to the connection of the cable with the elevator. Seals are effected between the sleeve and the wall and between the sleeve and the distal end of the cable with nipples of rigid tubing and an epoxy or elastomeric sealing material. A fine wire coil spring is disposed over the cable within the sleeve and is constrained between the nipples. The coil spring prevents abrasion of the sleeve from the cable and also prevents collapse of the sleeve.

11 Claims, 5 Drawing Figures

ENDOSCOPE FORCEPS ELEVATOR CABLE SEAL

BACKGROUND OF THE INVENTION

This invention relates generally to an endoscope or borescope, and is more particularly directed to a side-looking type of endoscope which is inserted into a body cavity and which directs an elongated forceps or other medical instrument laterally from the distanl end of the endoscope into the body cavity.

Endoscopes of this type employ a so-called elevator, which is a pivotally mounted block that is rocked, by means of a control cable, to divert the endoscope forceps from its axial orientation to a lateral orientation as its exits the head. Conventional endoscopes of this type do not have a sealed elevator cable, however. Instead, such endoscopes employ a metal-wrapped plastic tube that runs the full length of the endoscope insertion tube. The elevator control cable lies within this plastic tube. Body fluids and other fluids are allowed to enter this tube from the head. Then, after use, the tube is flushed from the control end of the insertion tube to wash out the control cable. This rather elaborate and labor intensive procedure complicates the endoscopic procedure considerably, and adds to the patient's expense.

OBJECTS AND SUMMARY OF THE INVENTION

It is an object of the present invention to provide an endoscope which avoids the prior art problems with respect to elevator control cables.

It is a more particular object of this invention to provide such an endoscope which avoids the requirement for a flushable control cable tube, and also avoids the complicated sealing and flushing system that is required in the control section of the conventional endoscopes.

It is another object of this invention to provide an endoscope in which body fluids are kept out of endoscope insertion tube, and which is easily cleansed after a procedure.

According to the principles of this invention, the elevator control cable is sealed at the endoscope head. To do this, the elevator control cable is enclosed in an elastomeric tubular sheath between a stationary part of the head and the moveable forceps elevator. This tubular sheath compresses in the axial direction as the cable is pulled through the head. A seal is provided at the head, i.e., at the proximal end of the sheath, by attaching the elastomeric tubular sheath around a nipple of rigid tubing, such as hypo tubing, through which the cable passes. This nipple enters a control cable aperture in the head, and is sealed to the head by means of an epoxy or an elastomer at the connection between the elastomeric tubular sheath and the rigid nipple. At the elevator end, i.e., distal end of the cable, a seal is effected by soldering or epoxying a nipple of rigid tubing, such as hypo tubing, to the cable. The elastomeric tubular sheath is then attached around the rigid tubing and is secured to the cable and to the nipple by means of an epoxy or elastomeric sealing material.

A fine wire spring, preferably of about 0.003 inch diameter wire, is situated over the cable and within the elastomeric tubing. This wire spring is constrained between the nipples, and therefore compresses as the elevator cable is withdrawn and the elevator raised. The spring wire is effectively stationary with respect to the elastomeric tubing, and prevents abrasion of the tubing by the cable. In addition, the spring wire prevents the tubing from buckling radially inward or collapsing against the cable.

The structure of this invention is particularly applicable to endoscopic retrograde cholangiopancreatography or ERCP endoscopes. These endoscopes are inserted into the small intestine through the mouth for visual inspection of the papilla of Vater, especially of the bile duct and pancreatic duct that empty into the small intestine. A fluoroscopic dye is injected through the endoscope so that the examining physician can look for abnormalities, such as gall stones, which can be removed through the bile duct using a thermal type instrument. Also, a drainage tube can be implanted, using the endoscope, into the papilla of Vater.

The improvement of this invention is particularly useful in this situation in preventing contamination of the endoscope from the associated body fluids, which can include infected bile or pancreatic fluids.

The above and many other objects, features, and advantages of this invention will be more fully understood from the ensuing detailed description of a preferred embodiment which should be considered in connection with the accompanying drawing.

DETAILED DESCRIPTION OF A PREFERRED EMBODIMENTS

Figure 1:
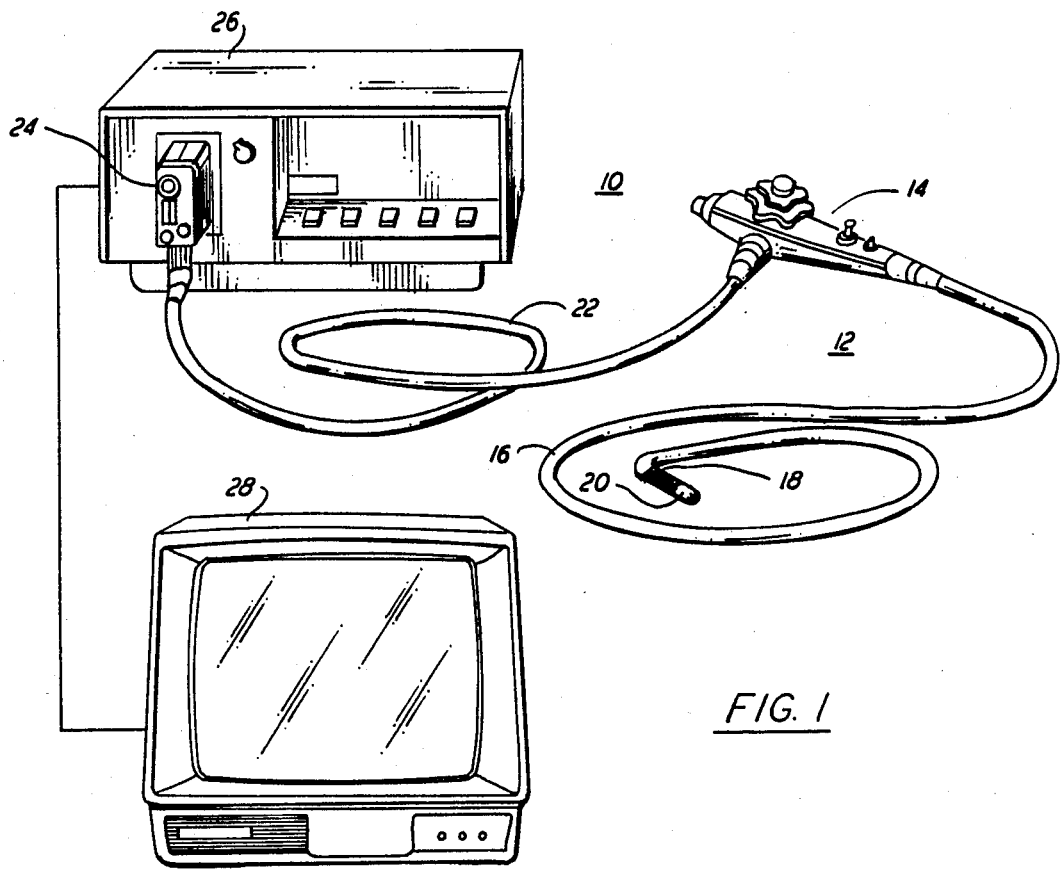
FIG. 1 is a perspective view of video endoscope apparatus embodying the principles of this invention.
Figure 3:
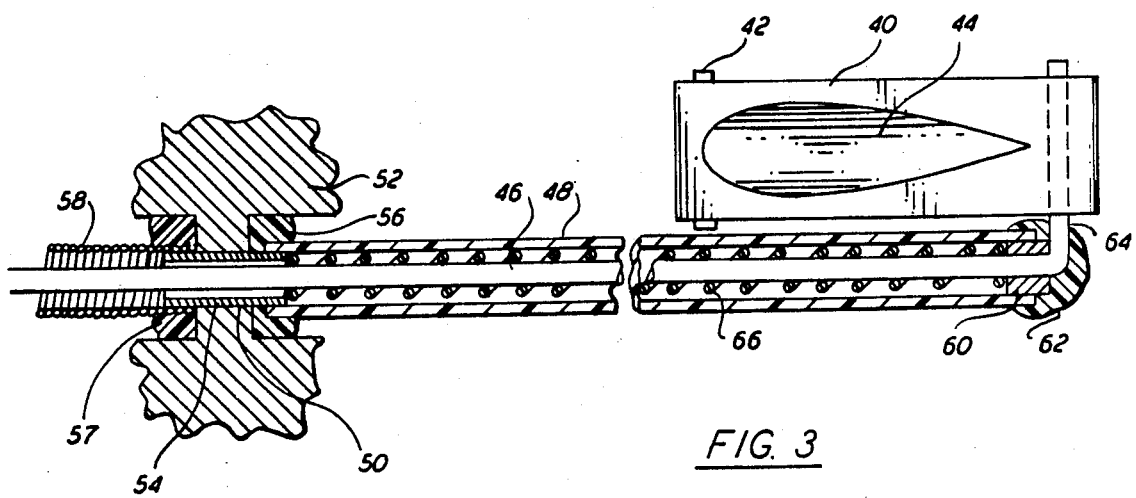
FIG. 3 is a detailed view of principal parts of the elevator mechanism of FIG. 2.

With reference to the drawing, and initially to FIG. 1, video endoscopic apparatus 10, here of the ERCP type, includes a video endoscope 12 formed of a control section 14, an elongated, flexible insertion tube 16, a bending or steering section 18 at the distal end of the insertion tube 16, and an endoscope head 20 at the tip of the bending section 18. An umbilical cord 22 extends from the control section 14 to an endoscope connector terminal 24 which plugs into a video processor 26. The latter is electrically connected to a video monitor 28 which provides a full color video image on a body cavity interior as seen from the point of view of the endoscope head 20.

The endoscope head 20 is of the side-looking type, which views the patient's body cavity laterally, i.e., radially of the insertion tube 16, and which is capable of inserting an endoscopic forceps or other elongated flexible instrument laterally and in the viewing direction. The head and its significant parts are illustrated in FIGS. 2-5.

Figure 2:
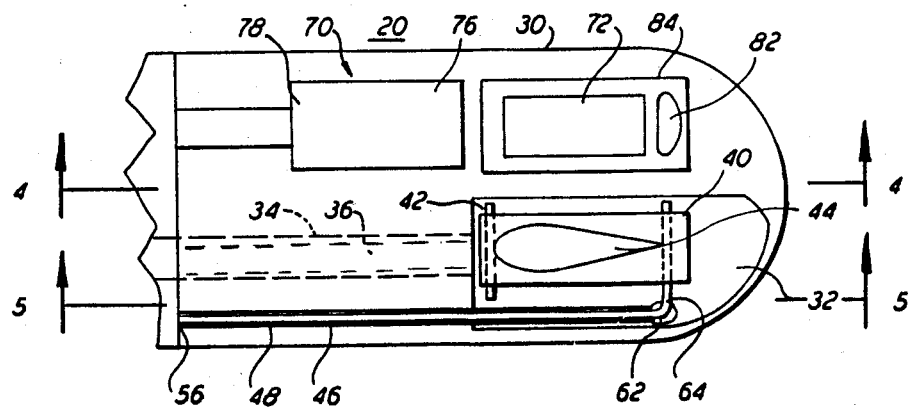
FIG. 2 is a plan view of the head of the endoscopic apparatus of the preferred embodiment.
Figure 5:
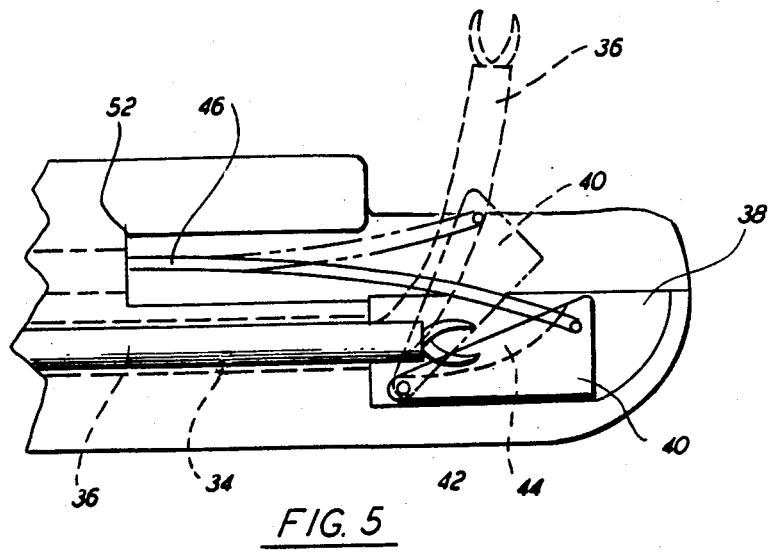

The head 20 is comprised of a shell or housing 30 with a cutout 32 at the right-hand side, that is, the lower half of the head 20 as illustrated in FIG. 2. A biopsy channel 34 which extends through the insertion tube 16 and bending section 18 passes also through the head shell 30 and guides a biopsy forceps 36 or other elongated flexible instrument into the patient's body cavity. A recess 38 in the cutout 32 contains a prism-shaped elevator 40, the same being mounted on a pivot 42 for rocking motion in and out of the drawing as shown in FIG. 2, or up and down as shown in FIG. 5. The elevator 40 has a rounded pocket 44 on its upper surface to divert the forceps 36 away from the endoscope axis.

A control cable or wire 46, preferably of a biocompatible metal such as stainless steel, is connected to the elevator 40 at a point spaced somewhat from the pivot 42, and is manipulated at the control section 14 to move the elevator 40, generally between the positions shown in solid line and in ghost in FIG. 5. The distal end portion of the control cable 46 is sheathed in a sleeve 48 of elastomeric tubing. The control cable 46 passes through an opening 50 in a fixed wall 52 of the shell 30 endoscope head 20, and the proximal end of the sleeve 48 is sealed to the wall 52 by means of a tubing nipple 54 disposed over the cable 46. The inside diameter of this nipple 54 is somewhat larger than the diameter of the cable 46 so that the cable 46 can pass freely through the nipple 54. The nipple 54 which projects somewhat on both the proximal and distal sides of the opening 50 is inserted into the proximal end of the sleeve 48. A sealing material 56, such as an epoxy sealant or an elastomeric sealant, seals the junction of the nipple 54 and the sleeve 48, and also forms a seal between the nipple 54 and the opening 50. Proximally beyond the wall 52, a conventional cable sheath 58 covers the cable 46 and can be secured to the proximal side of the nipple 54 by means of the fastening compound 57.

At the distal end of the sleeve 48, a nipple 60 of a rigid tubing, which can be, for example, hypo tubing or metal tubing, is soldered or otherwise affixed to the cable 46. The distal end of the sleeve 48 extends over this nipple 60 and a seal 62 of the sealing material is formed at the junction of the sleeve 48 and the nipple 60. An ell 64 formed in the distal end control cable 46 passes through the elevator 40 at the latter's distal end.

A fine wire coil spring 66 is situated within the sleeve 48 over the cable 46, and is constrained between the nipples 54 and 60. This coil spring 66 expands or compresses with the elastic material of the sleeve 48, so that there is substantially no relative movement between the spring 66 and the sleeve 48. This prevents abrasions of the sleeve 48 from cable movement, and further prevents collapse of the sleeve 48 against the cable 46.

Figure 4:
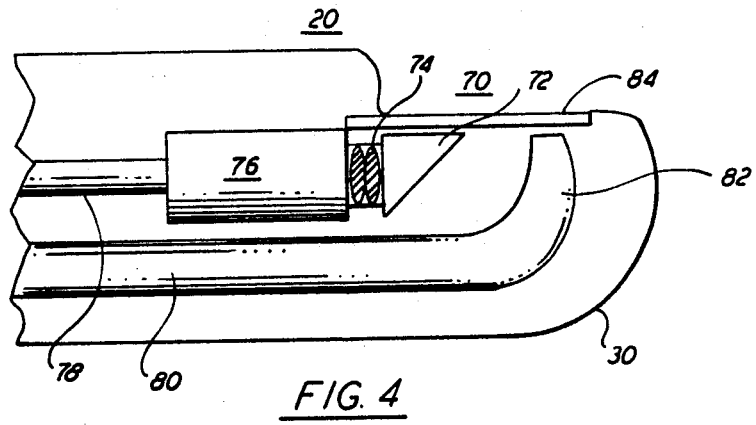
FIGS. 4 and 5 are side elevational views taken respectively along the lines 4—4 and 5—5 of FIG. 2.

To complete the disclosure, FIGS. 2 and 4 especially show side-looking optic system employed with the endoscope of this invention. Here, contained within the left side of the head 20 (i.e., at the top in FIG. 2) the optic system 70 has a reflecting prism 72 followed by focusing lenses 74 and an electronic imager 76. This imager can be, for example, of the type disclosed in U.S. Pat. No. 4,491,865 of Jan. 1, 1985. Transmission lines 78 pass from the imager 76 proximally back through the insertion tube, the control section 14, and the umbilical cord 22 to the video processor 26.

A fiber optic bundle 80 extends from the control section through the insertion tube and head 20 for illuminating the body cavity in the direction viewed through the prism 72. Here, the distal end 82 of the bundle 80 is bent and directed through a transparent cover plate 84 which also covers the prism 72. Although not specifically shown here, the fiber optic bundle 80 is preferably fanned out around the prism 72 so as to illuminate the body cavity evenly in the viewing direction.

As shown in FIG. 5, the forceps 36 is inserted through the biopsy channel 34 out into the recess 38 and against the pocket 44 of the elevator 40. The control cable 46 is manipulated to rock the elevator 40 up and down, in the sense shown in FIG. 5, as the forceps 36 is inserted. Thus, the combined rocking of the elevator 40 and the gradual insertion of the forceps 36 or other elongated flexible instrument, diverts the latter into the direction of viewing of the optics 70.

Because the structure of the head 20 leaves the opening 32 with the recess 38, the elevator 40 and the external part of the cable 46 exposed, the sheath 48 can be easily cleansed after an endoscopy procedure.

In a preferred embodiment, the elastomeric sleeve is formed of a silicon elastomer, preferably having a low durometer of about 50 Shore A. The sealing material used for the seals 56 and 62 can be of an adhesive elastomer, such as the type sold under the trademark Chemlok.

While a preferred embodiment has been described in detail hereinabove, it should be understood that the invention is not limited to that embodiment, and that many modifications and variations thereof would present themselves to those skilled in the art without departure from the scope and spirit of this invention, as defined in the appended claims.

I claim:

1. In an endoscope of the type employed for endoscopic examination of a patient's body cavity, comprising a flexible tubular member having a flexible outer sheath; a viewing head at the distal end of the tubular member, said head having at least one wall, including imaging means in said head for viewing from said head; a biopsy channel within said tubular member and extending to the distal end thereof and through said head, in which channel an elongated flexible instrument can be inserted to pass through said head into the body cavity; an elevator block rotatably mounted on said head for directing said flexible instrument emerging from said channel generally into the viewing direction of said imaging means, a control cable for said elevator block extending through said flexible tubular member through one said wall of said head and having a distal end connected to said elevator block to pivot the same selectively, an elastomeric sealing sleeve disposed over said cable with a proximal end at said wall and a distal end, and sealing means at the proximal and distal ends of the elastomeric sealing sleeve for hermetically sealing the proximal end of said sleeve with said wall and hermetically sealing the distal end of the sleeve with said cable; the improvement wherein said sealing sleeve is a tubular member of generally cylindrical shape, and further comprising antiabrasion means disposed within said elastomeric sealing sleeve and over said cable for permitting said sleeve to expand and contract axially with travel of said cable, while preventing said sheath from collapsing onto, and contacting said cable, thereby avoiding abrasion of said sleeve from said cable.

2. An endoscope as in claim 1 in which said antiabrasion means includes a wire coil disposed within the elastomeric sleeve and over said cable.

3. An endoscope as in claim 1 wherein said sealing means at the proximal end of said sleeve includes a rigid tubing nipple extending over said cable through said wall and extending into the proximal end of said sleeve, and a seal formed of sealing material the juncture of said tubing nipple and said sleeve.

4. An endoscope as in claim 3 wherein said sealing means at the distal end of the cable includes a rigid tubing nipple over said cable and affixed to said distal end thereof, the distal end of the sleeve extending over said nipple, and a seal formed of sealing material over the distal end of said sleeve and said nipple.

5. An endoscope as in claim 4 wherein said antiabrasion means includes a fine wire coil compression spring disposed over said cable and within said sleeve, with proximal and distal ends placed respectively against said nipples.

6. An endoscope as in claim 4 wherein said sealing material is an epoxy.

7. An endoscope as in claim 4 wherein said sealing material is an elastomeric seal.

8. An endoscope as in claim 4 wherein said rigid tubing nipple is soldered to the distal end of the cable.

9. An endoscope as in claim 1 wherein said sleeve comprises a silicon elastomeric tubing.

10. An endoscope as in claim 1 wherein said head is open in the region from said wall to said elevator block to facilitate washing thereof.

11. An endoscope as in claim 9 wherein said silicon elastomeric tubing has a durometer value less than about 70 Shore A.

* * * * *